United States Patent (10) Patent No.: US 11,071,817 B2
Evans et al. (45) Date of Patent: Jul. 27, 2021

(54) SYRINGE NEST ASSEMBLY

(71) Applicant: West Pharmaceutical Services, Inc., Exton, PA (US)

(72) Inventors: Christopher Evans, Long Valley, NJ (US); Brian Costello, Whitehouse Station, NJ (US); Raymond Protasiewicz, Whippany, NJ (US); Christopher Gieda, Long Valley, NJ (US)

(73) Assignee: WEST PHARMACEUTICAL SERVICES, INC., Exton, PA (US)

( * ) Notice: Subject to any disclaimer, the term of this patent is extended or adjusted under 35 U.S.C. 154(b) by 0 days.

(21) Appl. No.: 16/075,352

(22) PCT Filed: Feb. 8, 2017

(86) PCT No.: PCT/US2017/017031
§ 371 (c)(1),
(2) Date: Aug. 3, 2018

(87) PCT Pub. No.: WO2017/139385
PCT Pub. Date: Aug. 17, 2017

(65) Prior Publication Data
US 2019/0083697 A1 Mar. 21, 2019

Related U.S. Application Data

(60) Provisional application No. 62/292,607, filed on Feb. 8, 2016.

(51) Int. Cl.
*B65D 25/10* (2006.01)
*A61M 5/00* (2006.01)
(Continued)

(52) U.S. Cl.
CPC .............. *A61M 5/008* (2013.01); *B01L 9/54* (2013.01); *B32B 3/12* (2013.01); *B32B 3/30* (2013.01);
(Continued)

(58) Field of Classification Search
USPC ........................................ 206/363, 365, 366
See application file for complete search history.

(56) References Cited

U.S. PATENT DOCUMENTS 5,190,169 A * 3/1993 Sincock .............. A61M 5/3213
206/366
5,823,363 A 10/1998 Cassel
(Continued)

FOREIGN PATENT DOCUMENTS

DE 8707894 U1 8/1987
EP 2659979 A2 11/2013
WO 2014049714 A1 4/2014

OTHER PUBLICATIONS

International Search Report and Written Opinion dated May 15, 2017 in International Application No. PCT/US2017/017031.
(Continued)

*Primary Examiner* — Jacob K Ackun
(74) *Attorney, Agent, or Firm* — Panitch Schwarze Belisario & Nadel LLP

(57) ABSTRACT

A syringe nest assembly includes a base having a first surface and an opposing second surface and a first plate movably coupled to the base. The base includes a plurality of nesting units extending upwardly away from the first surface of the base. Each nesting unit includes a hollow body having a first open end distal from the first surface of the base and an opposing second open end. The first plate has a first surface and an opposing second surface. The first plate includes a plurality of apertures extending from the first
(Continued)

surface to the second surface of the first plate. Each aperture of the first plate is generally aligned with a respective nesting unit of the base.

15 Claims, 11 Drawing Sheets

(51) Int. Cl.
    *B01L 9/00*     (2006.01)
    *B32B 3/12*     (2006.01)
    *B32B 3/30*     (2006.01)
    *B32B 27/32*     (2006.01)
    *B32B 27/06*     (2006.01)
    *B32B 7/08*     (2019.01)

(52) U.S. Cl.
    CPC ............... *B32B 7/08* (2013.01); *B32B 27/06* (2013.01); *B32B 27/32* (2013.01); *B65D 25/108* (2013.01); *B32B 2250/02* (2013.01); *B32B 2274/00* (2013.01); *B32B 2535/00* (2013.01)

(56) References Cited

U.S. PATENT DOCUMENTS

| | | | |
|---|---|---|---|
| 5,975,295 A | 11/1999 | Diamond | |
| 7,665,491 B2* | 2/2010 | Lampropoulos | A61B 50/33 |
| | | | 141/311 A |
| 8,939,288 B2* | 1/2015 | Gagnieux | A61M 5/002 |
| | | | 206/366 |
| 2012/0118777 A1* | 5/2012 | Kakiuchi | A61M 5/002 |
| | | | 206/366 |
| 2015/0182686 A1* | 7/2015 | Okihara | B65D 77/2024 |
| | | | 206/366 |
| 2016/0121042 A1* | 5/2016 | Christensen | B65D 25/108 |
| | | | 206/366 |

OTHER PUBLICATIONS

International Preliminary Report on Patentability dated Jul. 6, 2018 in International Application No. PCT/US2017/017031.
Office Action dated Sep. 15, 2020 in Indian Application No. 201827030618.

* cited by examiner

SYRINGE NEST ASSEMBLY

This application is a section 371 of International Application No. PCT/US17/17031, filed Feb. 8, 2017, which was published Aug. 17, 2017 under International Publication No. WO 2017/139385 A1, which claims the benefit of U.S. Provisional Application No. 62/292,607, filed Feb. 8, 29016, the disclosures of which are incorporated herein by reference.

BACKGROUND OF THE INVENTION

The present invention relates to a syringe nest assembly. In particular, the present invention relates to a syringe nest assembly configured to more accurately center the syringes contained therein relative to each other and facilitate the syringes having the correct positioning when interfacing with automated manufacturing, handling packaging, and filling equipment.

A syringe nest is typically a substantially planar tray which sits in a syringe tub and has a plurality of individual nesting units, typically referred to as chimneys, each capable of receiving a syringe, to contain, transport and fill syringes in various manufacturing processes. The syringe nest is typically used in automation processes for the assembly of, for example, pre-filled syringes. The chimneys of a syringe nest have a defined center to center distance that must remain accurate, in order to ensure that the nest is compatible with existing manufacturing, packaging, and filling equipment. The quantity sizes of syringe nests have been increasing in recent years, with 160 chimneys/nest potentially becoming the new standard.

This has caused the syringe chimneys to be formed significantly closer together, particularly for nests requiring larger chimney diameters due to integrated safety systems. However, as the standard chimney diameter increases, it becomes more difficult to maintain the center to center distance which is necessary for ensuring that the syringes properly interface with existing automated manufacturing, handling, packaging, and filling equipment.

Accordingly, there is a need for a syringe nest assembly which ensures that the syringes positioned therein meet the standard requisite center to center distance.

BRIEF SUMMARY OF THE INVENTION

Briefly stated, in one embodiment, the present invention relates to a syringe nest assembly including a base having a first surface and an opposing second surface and a first plate movably coupled to the base. The base includes a plurality of nesting units extending upwardly away from the first surface of the base. Each nesting unit includes a hollow body having a first open end distal from the first surface of the base and an opposing second open end. The first plate has a first surface and an opposing second surface. The first plate includes a plurality of apertures extending from the first surface to the second surface of the first plate. Each aperture of the first plate is generally aligned with a respective nesting unit of the base.

In another embodiment, the present invention relates to a method of centering two or more syringes in a syringe nest assembly. The syringe nest assembly comprises a base having a first surface and an opposing second surface and a first plate movably coupled to the base. The base includes a plurality of nesting units extending upwardly away from the first surface of the base. Each nesting unit includes a hollow body having a first open end distal from the first surface of the base and an opposing second open end. The first plate has a first surface and an opposing second surface. The first plate includes a plurality of apertures extending from the first surface to the second surface of the first plate. Each aperture of the first plate is generally aligned with a respective nesting unit of the base. The method comprises positioning a first syringe in a first nesting unit and positioning a second syringe in a second nesting unit adjacent the first nesting unit, such that a barrel of each syringe extends through the hollow body of the respective nesting unit; and sliding the first plate in a first direction such that the first plate contacts each syringe and causes each syringe to move toward the interior wall surface of the respective nesting unit until each syringe contacts the interior wall surface of the respective nesting unit.

In another embodiment, the present invention relates to a syringe nest comprising a flexible base having a first surface and an opposing second surface. The base comprises a plurality of nesting units extending upwardly away from the first surface of the base. Each nesting unit comprises a hollow body having a first open end distal from the first surface of the base and an opposing second end. The base further comprises a notch formed at the second end of each nesting unit. Each notch is configured to be in a closed position when no syringe is positioned in the nesting unit and each notch is configured to be in an open position when a syringe is positioned in the nesting unit, such that the syringe extends through the base when the notch is in the open position.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
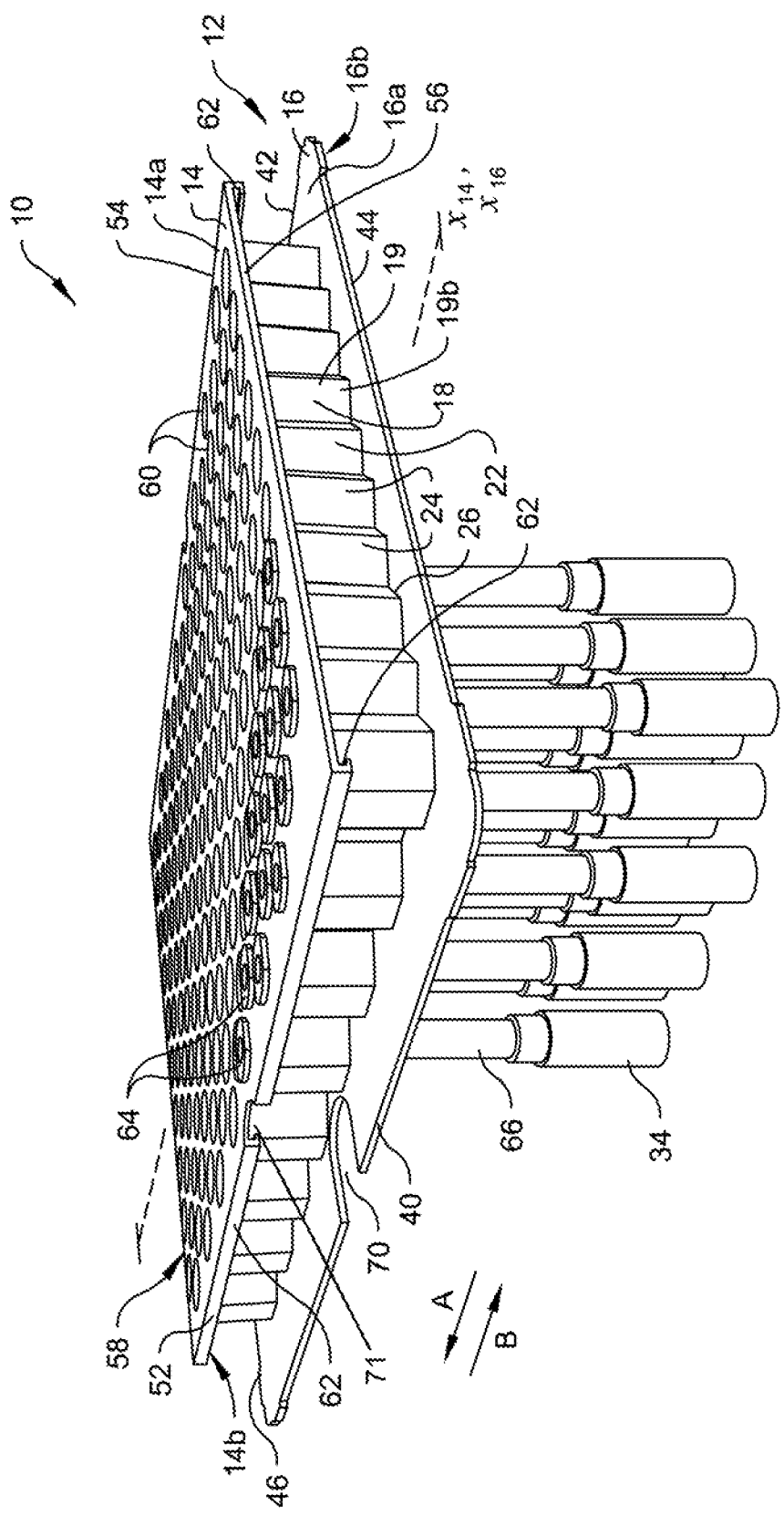
FIG. 1 is a top, front perspective view of a syringe nest assembly in accordance with an embodiment of the present invention.

Reference will now be made in detail to the present embodiments of the invention illustrated in the accompanying drawings. It should be noted that the drawings are in simplified form and are not drawn to precise scale. Certain terminology is used in the following description for convenience only and is not limiting. The words "right," "left," "top," "bottom" and "lower" designate directions in the drawings to which reference is made. The words "first," "second," "third" and "fourth" designate an order of operations in the drawings to which reference is made, but do not limit these steps to the exact order described. The words "inwardly" and "outwardly" refer to directions toward and away from, respectively, the geometric center of the assembly and designated parts thereof. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals and characters indicate like elements throughout, there are shown in FIGS. 1-8, presently preferred embodiments of syringe nest assemblies in accordance with the present invention. With reference initially to FIGS. 1-3B, the syringe nest assembly, generally designated 10, includes a syringe nest 12 and at least one movable plate 14.

Referring to FIG. 1, the nest 12 comprises a generally planar base or tray 16 having a first surface 16a and an opposing second surface 16b. The base 16 further includes a first edge or side 40 and an opposing second edge or side 42. The first and second edges 40, 42 extend parallel to each other. The base 16 further includes a third edge or side 44 and an opposing fourth edge or side 46. The third and fourth edges 44, 46 extend parallel to each other and perpendicular to the first and second edges 40, 42. A longitudinal axis $X_{16}$ of the base 16 extends parallel to the first and second edges 40, 42 from the third edge 44 toward the fourth edge 46 (or vice versa).

While the present embodiment is configured with the base 16 configured as a planar rectangular tray, the base 16 can alternatively be configured in any planar fashion suitable for its intended use, such as a planar circular, square, oval, or octagonal shaped tray.

The nest 12 further comprises a plurality of single nesting units, referred to herein as chimneys, 18. Each chimney 18 includes a generally hollow body 19 that extends distally from the first surface 16a of the base 16. The hollow body 19 includes a first open end 19a distal from the base 16 and a second open end 19b proximate the base 16. The hollow body 19 also includes an interior wall surface 20 and an exterior wall surface 22. The nest 12 can also include a syringe 34 received within each of the plurality of chimneys 18.

Figure 3A:
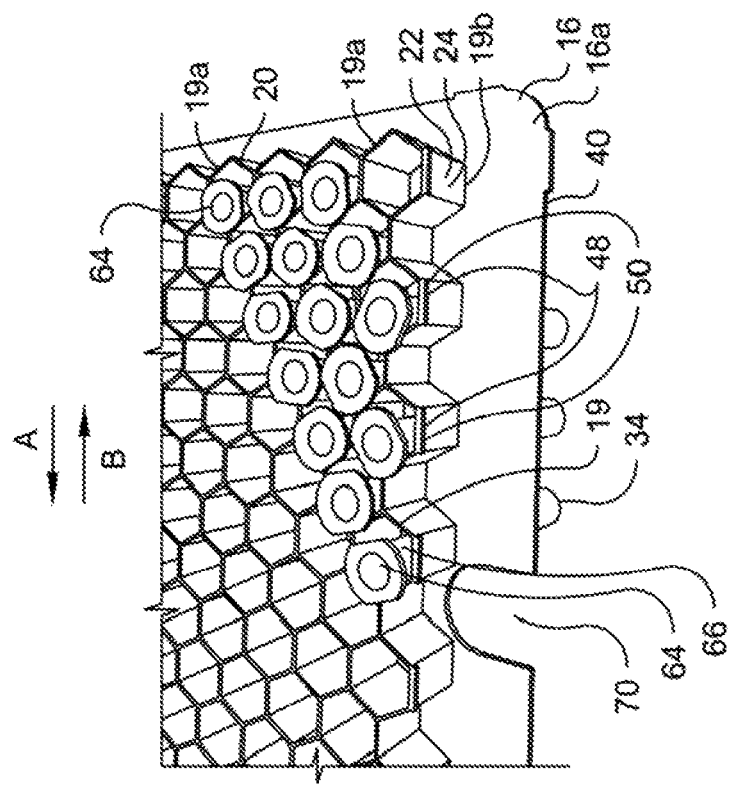
FIG. 3A is top, front partial perspective view of the syringe nest shown in FIG. 1 (with the top plate removed) with syringes in a first, un-centered position.
Figure 3B:
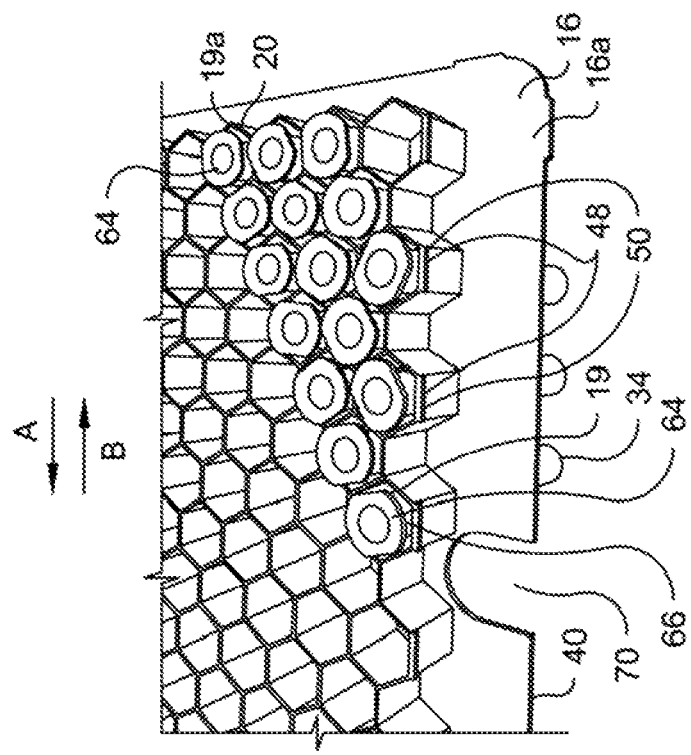
FIG. 3B is a top, front partial perspective view of the syringe nest assembly shown in FIG. 1 (with the top plate removed) with syringes in a second, centered position.

Referring to FIGS. 3A-3B, in one embodiment, each of the chimneys 18 preferably has a hexagonal shape or geometry. Thus, each chimney 18 has six sidewalls 24 and six connecting lines (also known as vertices or corners) 26. The hexagonal chimneys 18 are arranged in a honeycomb pattern. By the honeycomb pattern, the chimneys 18 are interconnected in such a manner that at least one sidewall 24, and preferably each sidewall 24, of one chimney 18 also forms a sidewall 24 of another chimney 18 (i.e., contiguous walls), such that no voids are formed between adjacent chimneys 18. Each chimney 18 thus shares at least one sidewall 24 with at least one other chimney 18. More preferably, with the exception of the outermost peripheral chimneys 18, every sidewall 24 of each chimney 18 is common to that of another chimney 18. Thus, each chimney 18 shares a common sidewall 24 with a plurality of other chimneys 18.

Conventionally, utilizing solely a honeycomb structure based on the desired center to center distance would require excessive wall thickness to form a platform on which flanges of the syringes may rest, which would be disadvantageous for injection molding. The present invention, however, avoids such excess wall thickness. In particular, each of the hexagonal chimneys 18 has a relatively large diameter that enables maintaining a predetermined center to center distance D of the syringes 34 contained therein, but also does not have an excessive sidewall 24 thickness.

It will, however, be understood that the chimneys 18 need not have a hexagonal geometry and need not be arranged in a honeycomb pattern. Indeed, the chimneys 18 may be cylindrical and arranged in any pattern, with or without gaps or voids between adjacent chimneys.

Referring to FIGS. 3A-3B, in one embodiment, each of the outermost chimneys 18 proximate the first edge 40 of the base 16 include a projecting protrusion, rim or flange 48 extending outwardly away from the chimney body 19 toward the first edge 40. More particularly, at the first open end 19a of each perimeter chimney 18 proximate the first edge 40, a portion of the chimney body 19 includes or is formed as a peripheral flange 48 which projects outwardly away from the chimney body 19 toward the first edge 40. In the case of hexagonal chimneys 18, the peripheral flange 48 is formed on one sidewall 24 at the first open end 19a of the chimney body 19.

Collectively, the peripheral flanges 48 of the outermost chimneys 18 proximate the first edge 40 define a first longitudinally extending peripheral flange 50, and more particularly a first peripheral flange 50 which extends along the first edge 40 of the base 16, in the plane of the first open ends 19a of the chimney bodies 19 and distal from the base 16. The first peripheral flange 50 extends along the longitudinal axis $X_{16}$ (i.e., from the third edge 44 toward the fourth edge 46 or vice versa). The first peripheral flange 50 comprises the spaced apart individual flanges 48 proximate the first edge 40, each of which extends along the longitudinal axis $X_{16}$ (i.e., from the third edge 44 toward the fourth edge 46 or vice versa).

Preferably, at the first open end 19a of each of the outermost chimneys 18 proximate the second edge 42 of the base 16, a portion of the chimney body 19 also includes or is formed as a peripheral protrusion or flange 48 which projects outwardly from the chimney body 19 toward the second edge 42. That is, a sidewall of each chimney 18 immediately adjacent the first and second edges 40, 42 includes a peripheral flange 48. Collectively, the peripheral flanges 48 of the outermost chimneys 18 proximate the second edge 42 define a second peripheral flange 50 which extends along the second edge 42 of the base 16, in the plane of the first open ends 19a of the chimney bodies 19 and distal from the base 16. The second peripheral flange 50 extends along the longitudinal axis $X_{16}$ (i.e., from the third edge 44 toward the fourth edge 46 or vice versa). Thus, the second peripheral flange 50 mirrors the first peripheral flange 50. The second peripheral flange 50 comprises the spaced apart individual flanges 48 proximate the second edge 42, each of which extends along the longitudinal axis $X_{16}$ (i.e., from the third edge 44 toward the fourth edge 46 or vice versa).

The plate 14 has a generally planar form and includes a first surface 14a and an opposing second surface 14b. In an assembled position of the syringe nest assembly 10, the second surface 14b faces the first surface 16a of the base 16. The plate 14 further includes a first edge or side 52 and an opposing second edge or side 54. The first and second edges 52, 54 extend parallel to each other. The plate 14 further includes a third edge or side 56 and an opposing fourth edge or side 58. The third and fourth edges 56, 58 extend parallel to each other and perpendicular to the first and second edges 52, 54. A longitudinal axis $X_{14}$ of the plate 14 extends parallel to the first and second edges 52, 54 from the third edge 56 toward the fourth edge 58 (or vice versa).

While the present embodiment is configured with the plate 14 configured as a planar rectangular form, the plate 14 can alternatively be configured into any planar fashion suitable for its intended use, such as a planar circular, square, oval, or octagonal shaped form. Preferably, however, the shape of the plate 14 conforms to that of the base 16.

The plate 14 further comprises a plurality of spaced apart openings or apertures 60 which extend from the first surface 14a to the second surface 14b. The apertures 60 are defined by sidewalls 61 extending through the body of the plate 14 from the first surface 14a to the second surface 14b. The position of each aperture 60 corresponds to (i.e., is configured to be aligned with) a respective one of the chimneys 18 of the nest 12. The apertures 60 may have any geometric shape. Preferably, the apertures 60 are cylindrical (e.g., circular in cross-section). However, it will be understood that the apertures 60 may alternatively be hexagonal or any other shape which complements the shape of the associated chimney 18.

In one embodiment, the first edge 52 of the plate 14 includes a first elongated slot or groove 62 configured to mate with the first peripheral flange 50 (i.e., the individual flanges 48 of the peripheral chimneys 18) of the base 16. More particularly, the first edge 52 of the plate 14 is provided with an L-shaped form which extends downwardly from the first edge 52 and defines the first elongated slot 62 therein. The first elongated slot 62 extends along the longitudinal axis $X_{14}$ of the plate 14 (i.e., from the third edge 56 toward the fourth edge 58 or vice versa). The first peripheral flange 50 of the perimeter chimneys 18 of the first edge 40 of the nest 12 is received and movable within the first elongated slot 62. By this engagement, the plate 14 is slidable relative to the nest 12, and more particularly the base 16 and chimneys 18.

Preferably, the second edge 54 of the plate 14 includes a second elongated slot or groove 62 configured to mate with the second peripheral flange 50 of the base 16. More particularly, the second edge 54 of the plate 14 is provided with an L-shaped form which extends downwardly from the second edge 54 and defines the second elongated slot 62 therein. The second elongated slot 62 extends along the longitudinal axis $X_{14}$ of the plate 14 (i.e., from the third edge 56 toward the fourth edge 58 or vice versa). The second peripheral flange 50 of the perimeter chimneys 18 of the second edge 42 of the nest 12 is received and movable within the second elongated slot 62. By this engagement, the plate 14 is slidable relative to the nest 12, and more particularly the base 16 and chimneys 18.

More particularly, the plate 14 is slidable in a first direction A or an opposing second direction B relative to the nest 12, the first and second directions being parallel to the longitudinal axes $X_{14}$, $X_{16}$ of the plate 14 and base 16, respectively. As described in further detail below, by this sliding movement, the plate 14 can move the syringes 34 in order to maintain a predetermined center to center distance D between the syringes 34 placed within each chimney 18 (e.g., as required by manufacturers) (see FIGS. 2B and 3B). The predetermined center to center distance D refers to the distance between a center C of a syringe 34 arranged in one chimney 18 and a center C of a syringe 34 arranged in an adjacent chimney 18.

It will be understood by those skilled in the art that the first and second peripheral flanges 50 of the base 16 need not be formed along the first and second edges 40, 42 of the base 16 and the corresponding first and second elongated slots 62 need not be formed along the first and second edges 52, 54 of the plate 14. Instead, the flanges and slots may be formed along the third and fourth edges 44, 46 and 56, 58 of the base 16 and plate 14, such that the plate 14 is slidable in a third or fourth direction which are perpendicular to the first and second directions A, B (i.e., directions perpendicular to the longitudinal axes $X_{14}$, $X_{16}$ of the plate 14 and base 16, respectively). Alternatively, the flanges may be formed proximate certain edges 52, 54, 56, 58 of the plate 14, while the slots are formed proximate corresponding edges 40, 42, 44, 46 of the base 16.

Figure 2A:
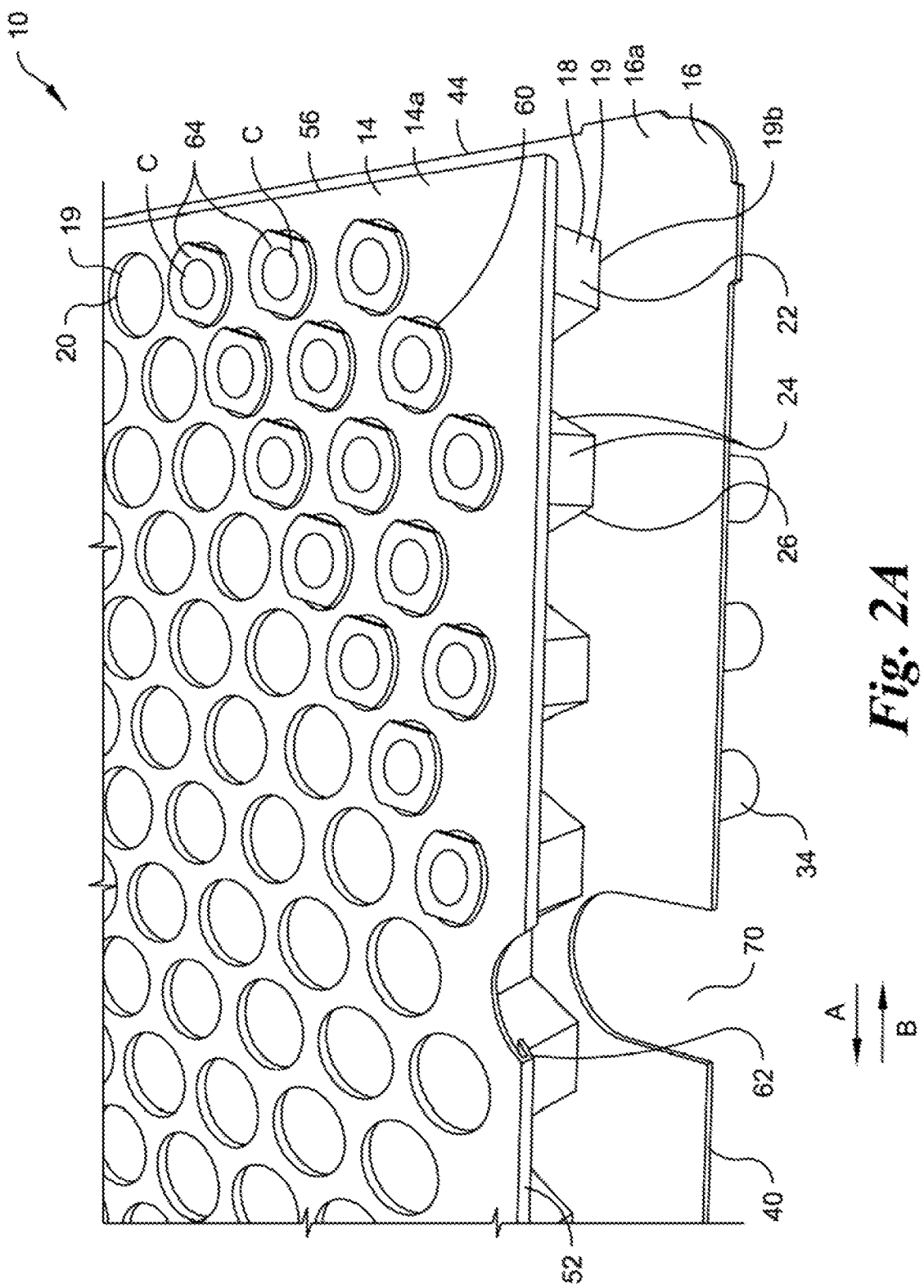
FIG. 2A is a top, front partial perspective view of the syringe nest assembly shown in FIG. 1 with syringes in a first, un-centered position.

In a first, assembled position of the syringe nest assembly 10, as shown in FIG. 2A, the plate 14 is coupled to the nest 12, such that the first and second peripheral flanges 50 of the base 16 are received within the first and second elongated slots 62 of the plate 14. As such, the plate 14 and the base 16 are movable, and more particularly slidable, relative to each other along the longitudinal axes $X_{14}$, $X_{16}$. A syringe 34 is positioned within one or more of the apertures 60 and corresponding chimneys 18 of the assembly 10. However, the syringes 34 are not properly centered, meaning they are not positioned so as to maintain the predetermined center to center distance D between adjacent syringes 34.

In one embodiment, in the assembled position, a flange 64 of each syringe 34 is positioned above the plane of the plate 14 and a barrel 66 of each syringe 34 is positioned within (and extends through) an aperture 60 of the plate 14 and a corresponding chimney 18 of the nest 12. The flange 64 of each syringe 34 may either rest on the first surface 14a of the plate 14 or may be proximate to but not in contact with the first face 14a.

In another embodiment, in the assembled position, the flange 64 of each syringe 34 is positioned within an aperture 60 of the plate 14 (e.g., within a counterbore) and the barrel 66 of each syringe is positioned within (and extends through) a corresponding chimney 18 of the nest 12.

Figure 2B:
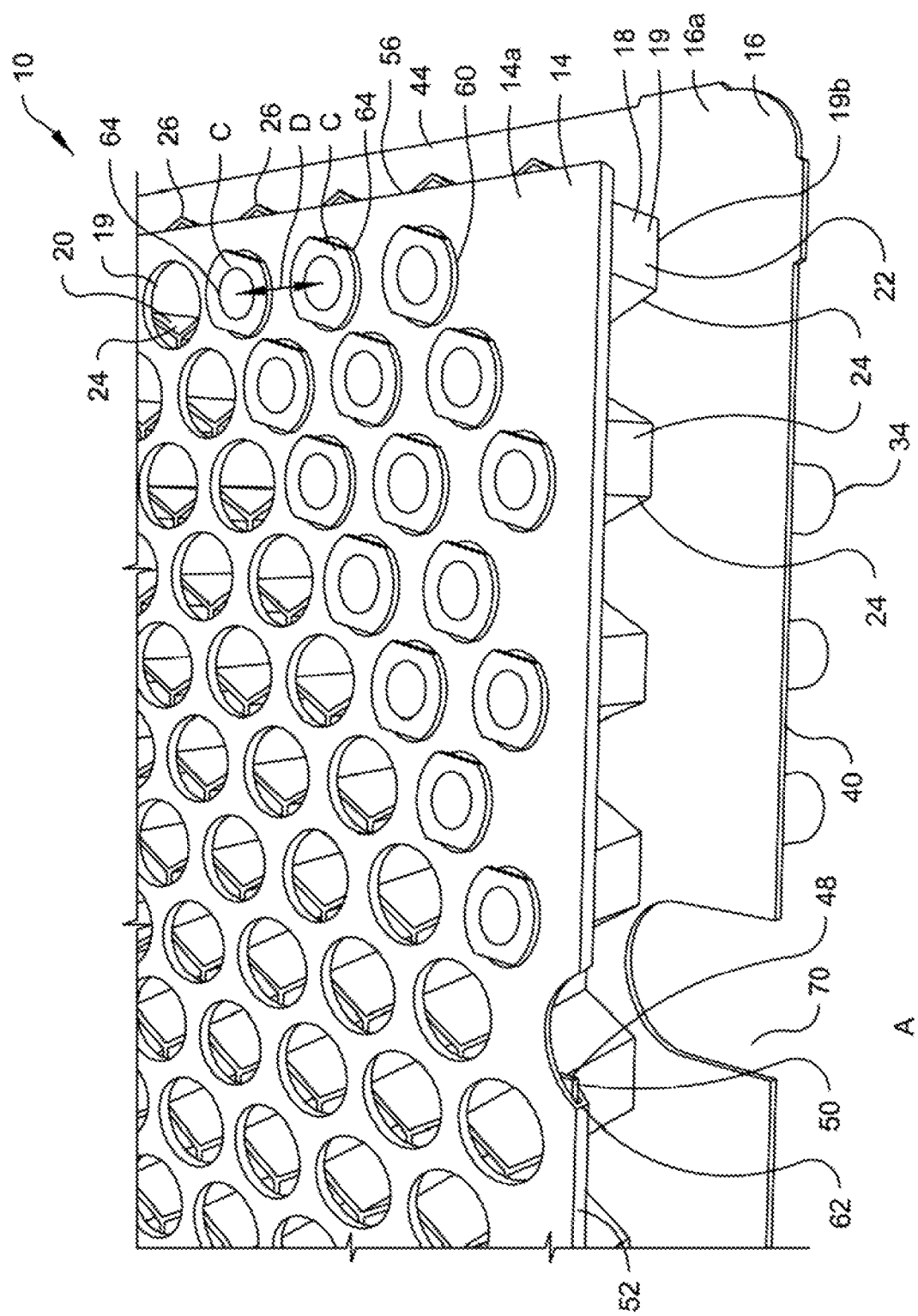
FIG. 2B is a top, front partial perspective view of the syringe nest assembly shown in FIG. 1 with syringes in a second, centered position.

To place syringe nest assembly 10 in a second position, in which the syringes 34 are in the predetermined center to center distance D, the plate 14 moves, and more particularly, slides in the first direction A along the longitudinal axis $X_{14}$. The sliding movement of the plate 14 causes the inner sidewall 61 of the apertures 60 of the plate 14 to come into contact with either the barrel 66 or the flange 64 of the syringe 34 positioned therein. By this contact, the plate 14 causes the syringe 34 to move with the plate 14 in the first direction A toward the interior wall surface 20 of the respective chimney 18. The sliding movement of the plate 14 and syringes 34 continues until the barrel 66 of each syringe 34 abuts or contacts a portion of the interior wall surface 20 of the chimney 18 in which the syringe 34 is positioned (see FIGS. 2B and 3B). Thus, the second position of the syringe nest assembly 10, as shown in FIGS. 2B and 3B, is attained, wherein the syringes 34 are positioned according to the requisite center to center distance D.

Figure 4A:
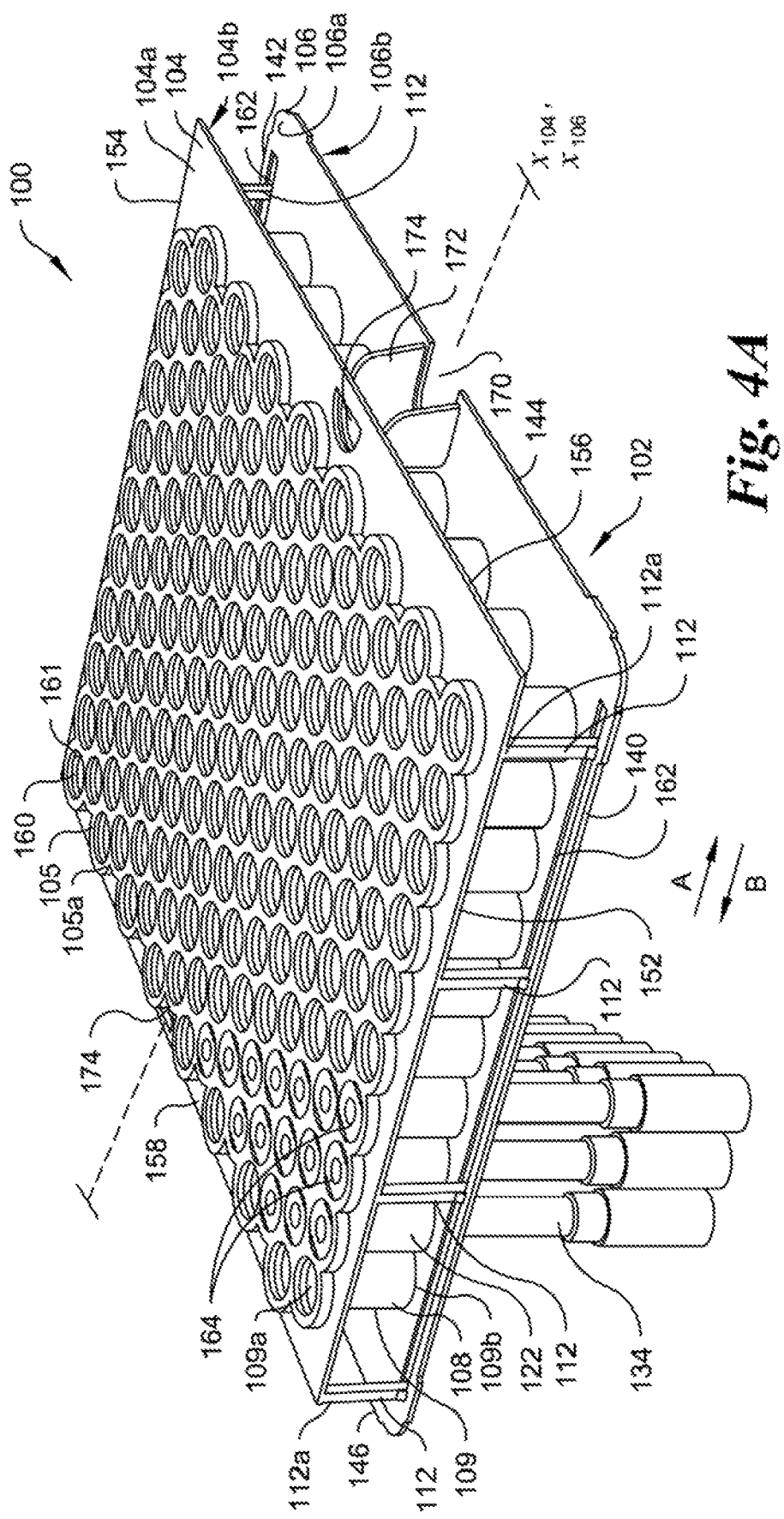
FIG. 4A is a top, front perspective view of a syringe nest assembly in accordance with a second embodiment of the present invention, with the assembly being shown with syringes in a first, un-centered position.
Figure 4B:
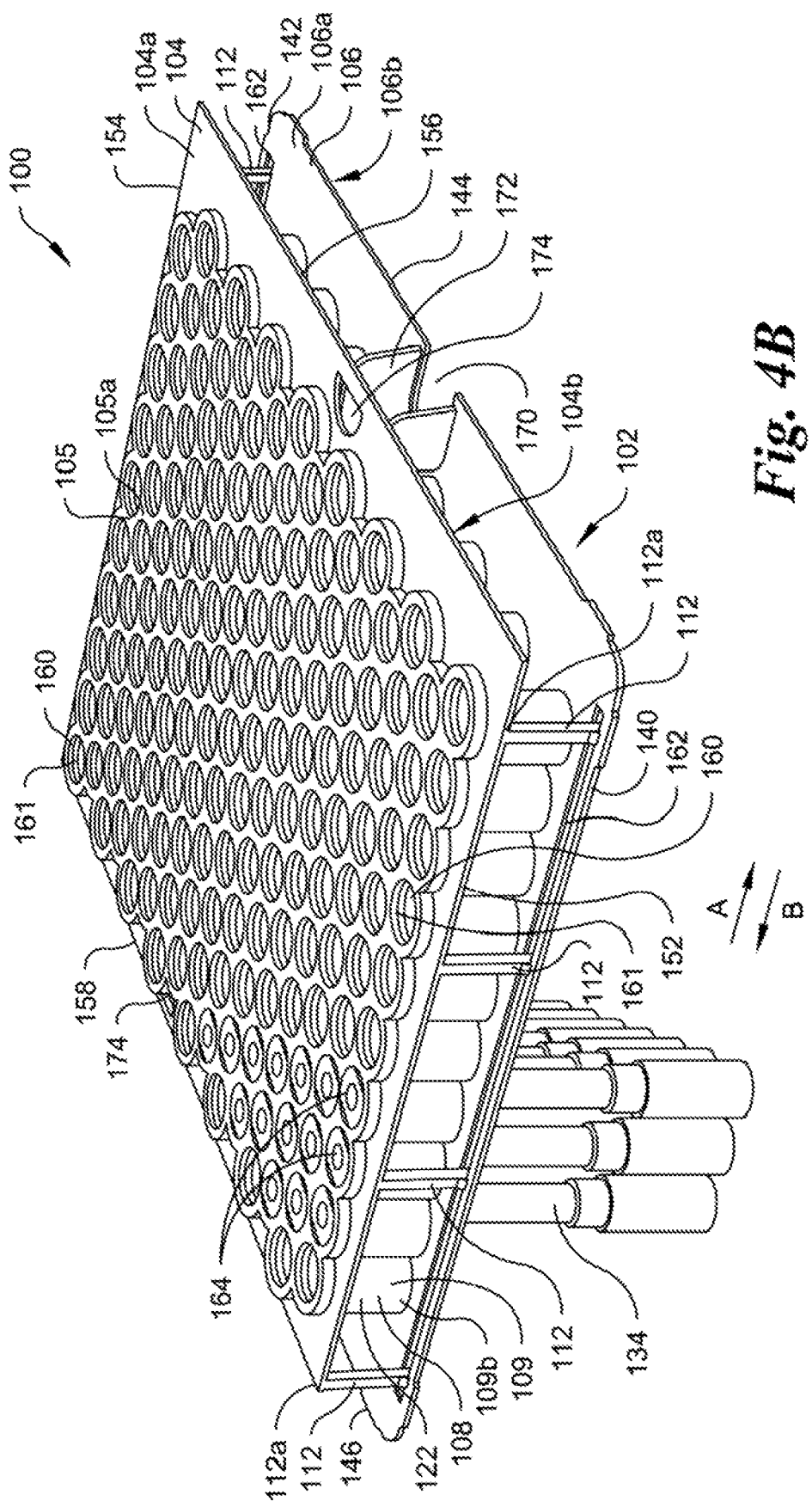
FIG. 4B is a top, front perspective view of the syringe nest assembly shown in FIG. 4A with syringes in a second, centered position.
Figure 5:
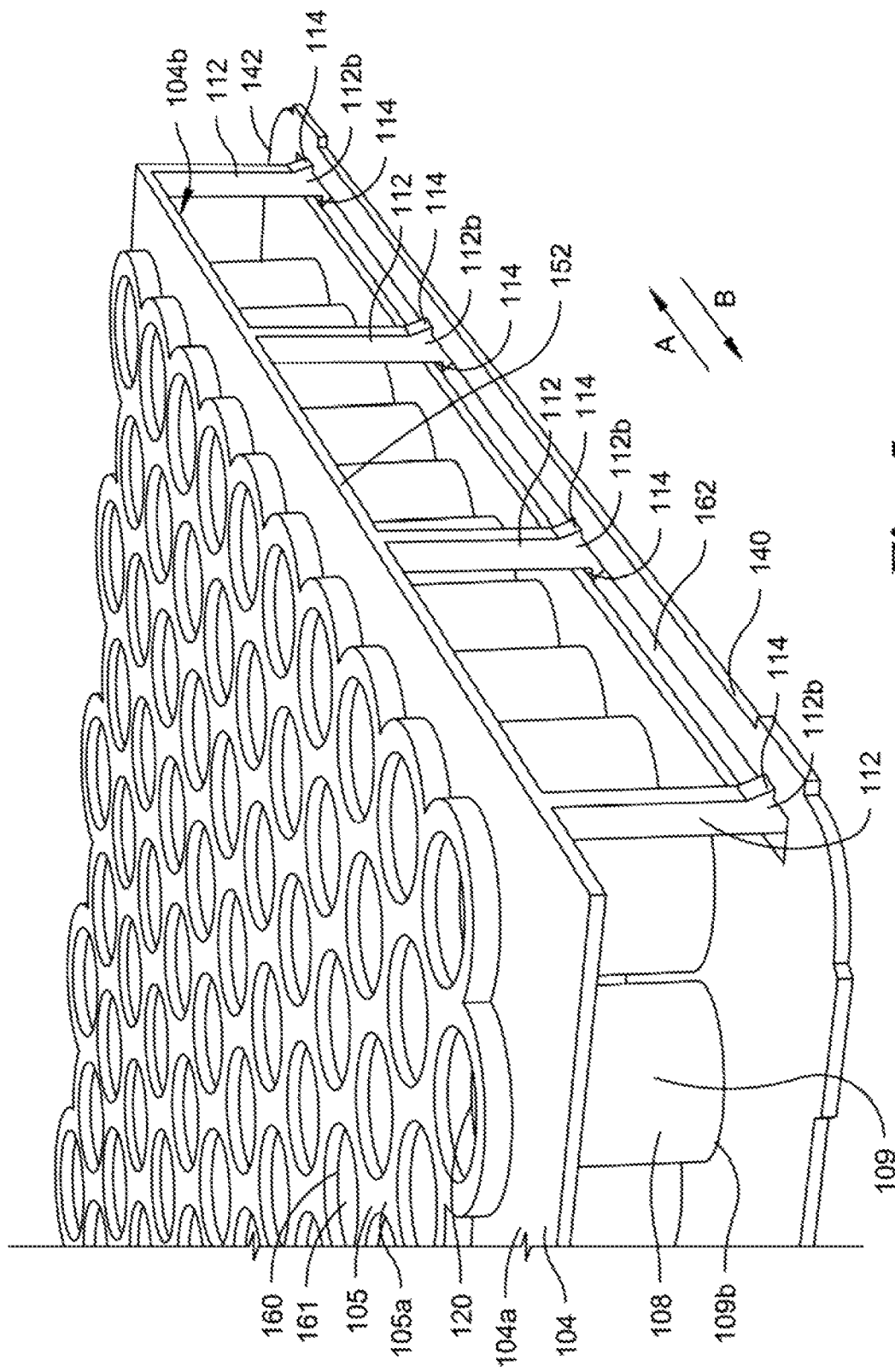
FIG. 5 is an enlarged top, side partial perspective view of the syringe nest assembly shown in FIGS. 4A-4B.

FIGS. 4A-5 depict another embodiment of a syringe nest assembly 100 according to the present invention. The syringe nest assembly 100 is generally similar to the syringe nest assembly 10 of FIGS. 1-3B, except in certain aspects as discussed below.

Referring to FIGS. 4A-4B, the syringe nest assembly 100 includes a syringe nest 102 and at least one movable plate 104. The nest 102 comprises a generally planar base or tray 106 having a first surface 106a and an opposing second surface 106b. The base 106 further includes a first edge or side 140 and an opposing second edge or side 142. The first and second edges 140, 142 extend parallel to each other. The base 106 further includes a third edge or side 144 and an opposing fourth edge or side 146. The third and fourth edges 144, 146 extend parallel to each other and perpendicular to the first and second edges 140, 142. A longitudinal axis $X_{106}$ of the base 106 extends parallel to the first and second edges 140, 142 from the third edge 144 toward the fourth edge 146 (or vice versa).

The base 16 is preferably configured as a planar rectangular tray, but can alternatively be configured in any planar fashion suitable for its intended use, such as a planar circular, square, oval, or octagonal shaped tray.

The nest 102 further comprises a plurality of chimneys 108, and more preferably a plurality of spaced-apart chimneys 108 (i.e., there is a gap between adjacent chimneys 108). However, it will be understood that the chimney 108 may be arranged in any pattern, such as, for example, the honeycomb pattern described with respect to FIGS. 1-3B.

Each chimney 108 includes a generally hollow body 109 that extends distally from the first surface 106a of the base 106. The hollow body 109 includes a first open end 109a distal from the base 106 and a second open end 109b proximate the base 16. The hollow body 109 also includes an interior wall surface 120 and an exterior wall surface 122. The nest 102 can also include a syringe 134 received within each of the plurality of chimneys 108.

Referring to FIGS. 4A-5, in one embodiment, each of the chimneys 108 preferably has a cylindrical shape or geometry. However, it will be understood that the chimneys 108 may have any suitable shape or geometry, such as, for example, the hexagonal geometry discussed above with respect to FIGS. 1-3B.

Referring to FIGS. 4A-5, in one embodiment, the base 106 includes a first elongated slot 162 formed proximate to or at the first edge 140. The first elongated slot 162 preferably extends along the longitudinal axis $X_{106}$ of the base 106 (i.e., from proximate the third edge 144 toward the fourth edge 146 or vice versa). The base 106 further preferably includes a second elongated slot 162 formed proximate to or at the second edge 142 which similarly extends along the longitudinal axis $X_{106}$ of the base 106.

The plate 104 has a generally planar form and includes a first surface 104a and an opposing second surface 104b. In an assembled position of the syringe nest assembly 100, the second surface 104b faces the first surface 106a of the base 106. The plate 104 further includes a first edge or side 152 and an opposing second edge or side 154. The first and second edges 152, 154 extend parallel to each other. The plate 104 further includes a third edge or side 156 and an opposing fourth edge or side 158. The third and fourth edges 156, 158 extend parallel to each other and perpendicular to the first and second edges 152, 154. A longitudinal axis $X_{104}$ of the plate 104 extends parallel to the first and second edges 152, 154 from the third edge 156 toward the fourth edge 158 (or vice versa).

While the plate 104 is preferably configured as a planar rectangular form, the plate 104 can alternatively be configured into any planar fashion suitable for its intended use, such as a planar circular, square, oval, or octagonal shaped form. Preferably, however, the shape of the plate 104 conforms to that of the base 106.

The plate 104 further comprises a central raised portion 105. The central raised portion 105, has a distal surface 105a extending in a plane that is above the plane of the first surface 104a of the plate 104. The plate 104 further comprises plurality of openings or apertures 160 which extend through the body of the plate 104, and more particularly from the distal surface 105a of the raised portion 105 to the second surface 104b of the plate 104. The apertures 160 are defined by sidewalls 161 extending through the body of the plate 104, and more particularly from the distal surface 105a of the raised portion 105 to the second surface 104b of the plate 104. The position of each aperture 160 corresponds to (i.e., is aligned with) a respective one of the chimneys 108 of the nest 102. The apertures 160 may have any geometric shape. Preferably, the apertures 160 are cylindrical (e.g., circular in cross-section). However, it will be understood that the apertures 160 may alternatively be hexagonal or any other shape which complements the shape of the associated chimney 108.

The plate 104 further preferably comprises at least one post 112, and more preferably a plurality of spaced-apart posts 112. More particularly, a plurality of spaced-apart posts 112 are preferably formed or otherwise provided proximate to or at the first edge 152 of the plate 104. Preferably, a plurality of spaced-apart posts 112 are also formed or otherwise provided proximate to or at the second edge 154 of the plate 104.

Each post 112 has a first proximal end 112a and an opposing second distal end 112a. The first proximal end 112a is preferably attached to or integrally formed with the plate 104, and more preferably the second surface 104b of the plate 104. The distal end 112a of each post 112 is distal from the plate 104. Thus, each post 112 is a downwardly facing post. It will be understood by those skilled in the art that the term "post" is used herein for merely illustrative purposes, and may easily be replaced by another appropriate term, such as pin, tab, protrusion, bar, and the like.

Referring to FIG. 5, the distal end 112a of each post 112 is preferably movably coupled to the base 106, and more particularly one of the elongated slots 162 of the base 106. More particularly, the distal end 112a of each post 112 includes first and second tongues 114. The first tongue 114 protrudes outwardly away from the body of the post 112 in a first direction, while the second tongue 114 protrudes outwardly away from the body of the post 112 in a second direction opposite of the first direction. Each post 112, and more particularly the distal end 112a of each post 112, formed proximate the first edge 152 of the plate 104 is configured to mate with the first elongated slot 162 of the base 106. Each post 112, and more particularly the distal end 112a of each post 112, formed proximate the second edge 154 of the plate 104 is configured to mate with the second elongated slot 162 of the base 106. More particularly, in the mated configuration, the distal end 112a of each post 112 engages one of the elongated slots 162, such that one of the first and second tongues 114 extends towards the first edge 140 of the base 106 and engages the first surface 106a of the base 106, while the other one of the first and second tongues 114 extends away from the first edge 140 of the base 106 and engages the second surface 106b of the base 106.

The posts 112 of the plate 104 are thus received and movable within the first and second elongated slots 162 of the base 106. By this engagement, the plate 104 is slidable relative to the nest 102, and more particularly the base 106 and chimneys 108. More particularly, the plate 104 is slidable in a first direction A or an opposing second direction B relative to the nest 102, the first and second directions being parallel to the longitudinal axes $X_{104}$, $X_{106}$ of the plate 104 and base 106, respectively.

It will be understood by those skilled in the art that the first and second elongated slots 162 of the base 106 need not be formed along the first and second edges 140, 142 of the base 106 and the corresponding posts 112 of the plate 104 need not be formed along the first and second edges 152, 154 of the plate 104. Instead, the slots and posts may be formed along the third and fourth edges 144, 146 and 156, 158 of the base 106 and plate 104, such that the plate 104 is slidable in a third or fourth direction which are perpendicular to the first and second directions A, B (i.e., directions perpendicular to the longitudinal axes $X_{104}$, $X_{106}$ of the plate 104 and base 106, respectively).

In a first, assembled position of the syringe nest assembly 100, as shown in FIG. 4A, the plate 104 is coupled to the nest 102, such that the distal ends 112a of the posts 112 of the plate 104 are received within the first and second elongated slots 162 of the base 106. As such, the plate 104 and the base 106 are movable, and more particularly slidable, relative to each other along the longitudinal axes $X_{104}$, $X_{106}$. A syringe 134 is positioned within one or more of the apertures 160 and corresponding chimneys 108 of the assembly 100. However, the syringes 134 are not properly centered, meaning they are not positioned so as to maintain the predetermined center to center distance D between adjacent syringes 134.

In one embodiment, in the assembled position, a flange 164 of each syringe 134 is positioned within an aperture 160 of the plate 104 and a barrel 166 of each syringe 134 is positioned within (and extends through) a corresponding chimney 108 of the nest 102. Each aperture 160 includes a counterbore which captures the syringe flange 164 therein on both the top and bottom sides of the flange 164, which allows for better control of the skewness of the syringes 134.

In another embodiment (not shown), the flange, 164 of each syringe 134 is positioned above the plane of the raised portion 105 of the plate 104 and the barrel 166 of each syringe 134 is positioned within (and extends through) an aperture 160 of the plate 104 and a corresponding chimney 108 of the nest 102. The flange 164 of each syringe 134 may either rest on the distal surface 105a of the raised portion 105 of the plate 104 or may be proximate to but not in contact with the distal surface 105a. In another embodiment, the plate 104 does not include the raised portion 105, such that the flange 164 of each syringe 134 rest on the first surface 104a of the plate 104 or is proximate to but not in contact with the first surface 104a.

To place the syringe nest assembly 100 in a second position, shown in FIG. 4B, in which the syringes 134 are in the predetermined center to center distance D, the plate 104 moves, and more particularly, slides in the first direction A along the longitudinal axis $X_{104}$. The sliding movement of the plate 104 causes the inner sidewall 161 of the apertures 160 to come into contact with the flange 164 (or the barrel 166) of the syringe 134 positioned therein. By this contact, the plate 104 causes the syringe 134 to move with the plate 104 in the first direction A toward the interior wall surface 120 of the respective chimney 108. The sliding movement of the plate 104 and syringes 134 continues until the barrel 166 of each syringe 134 abuts or contacts a portion of the interior wall surface 120 of the chimney 108 in which the syringe 134 is positioned. Thus, the second position of the syringe nest assembly 100, as shown in FIG. 4B, is attained, wherein the syringes 134 are positioned according to the requisite center to center distance D.

Figure 6A:
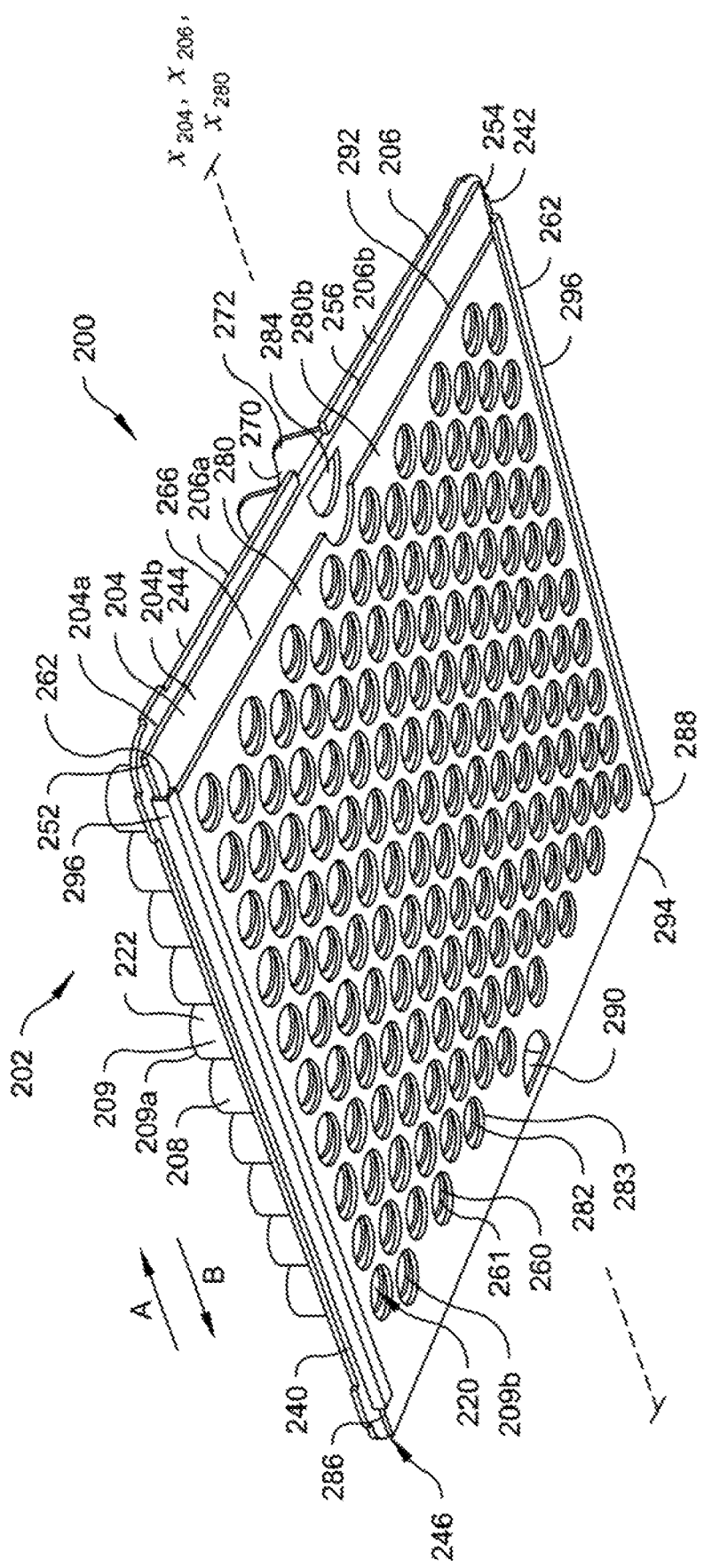
FIG. 6A is a bottom, front perspective view of a syringe nest assembly in accordance with a third embodiment of the present invention, with the assembly being shown in a first position in which syringes would not be centered.
Figure 6B:
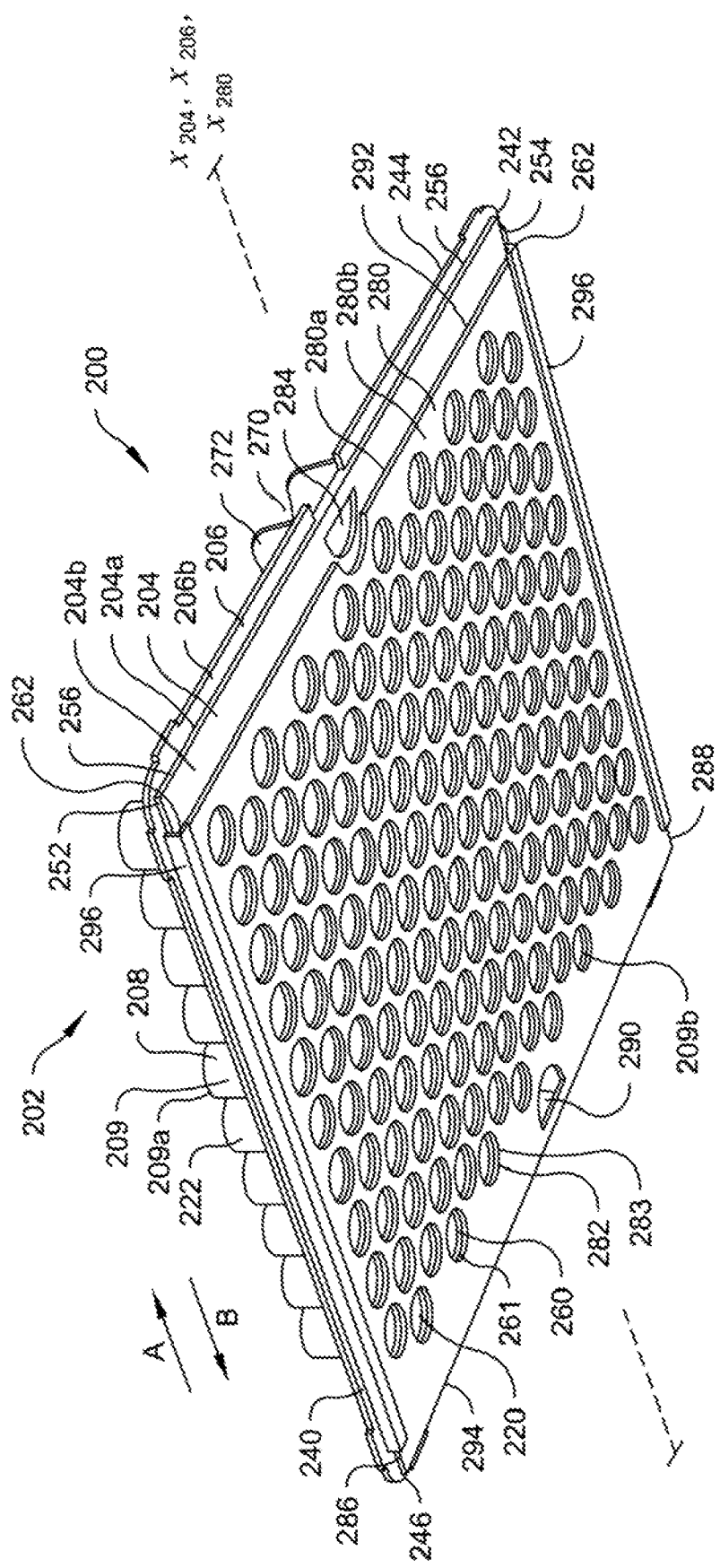
FIG. 6B is a bottom, front perspective view of the syringe nest assembly shown in FIG. 6A in a second position in which syringes would be centered relative to each other.

FIGS. 6A-6B depict another embodiment of a syringe nest assembly 200 according to the present invention. The syringe nest assembly 200 is generally similar to the syringe nest assembly 10 of FIGS. 1-3B, except in certain aspects as discussed below.

Referring to FIGS. 6A-6B, the syringe nest assembly 200 includes a syringe nest 202 and at least one movable plate 204. More preferably, the syringe nest assembly 200 includes a first movable plate 204 and a second movable plate 280. The nest 202 is generally similar to the syringe nest 102 of FIGS. 4A-5, except in certain aspects as discussed below. The nest 202 comprises a generally planar base or tray 206 having a first surface 206a and an opposing second surface 206b. The base 206 further includes a first edge or side 240 and an opposing second edge or side 242. The first and second edges 240, 242 extend parallel to each other. The base 206 further includes a third edge or side 244 and an opposing fourth edge or side 246. The third and fourth edges 244, 246 extend parallel to each other and perpendicular to the first and second edges 240, 242. A longitudinal axis $X_{206}$ of the base 206 extends parallel to the first and second edges 240, 242 from the third edge 244 toward the fourth edge 246 (or vice versa).

The base 206 is preferably configured as a planar rectangular tray, but can alternatively be configured in any planar fashion suitable for its intended use, such as a planar circular, square, oval, or octagonal shaped tray.

The nest 202 further comprises a plurality of chimneys 208, and more preferably a plurality of spaced-apart chimneys 208 (i.e., there is a gap between adjacent chimneys 208). However, it will be understood that the chimney 208 may be arranged in any pattern, such as, for example, the honeycomb pattern described with respect to FIGS. 1-3B.

Each chimney 208 includes a generally hollow body 209 that extends distally from the first surface 206a of the base 206. The hollow body 209 includes a first open end 209a distal from the base 206 and a second open end 209b proximate the base 206. The hollow body 209 also includes an interior wall surface 220 and an exterior wall surface 222. The nest 202 can also include a syringe (not shown) received within each of the plurality of chimneys 208.

Referring to FIGS. 6A-6B, in one embodiment, each of the chimneys 208 preferably has a cylindrical shape or geometry. However, it will be understood that the chimneys 208 may have any suitable shape or geometry, such as, for example, the hexagonal geometry discussed above with respect to FIGS. 1-3B.

In one embodiment, a first L-shaped member 296 is provided proximate to or at the first edge 240 of the base 206. Preferably, a second L-shaped member 296 is also provided proximate to or at the second edge 242 of the base 206. Each L-shaped member 296 extends downwardly from the bottom surface 206b of the base 206 and defines a first elongated slot or groove 262 therein. Each L-shaped member 296 and each elongated slot 262 extend along the longitudinal axis $X_{206}$ of the base 206 (i.e., from the third edge 244 toward the fourth edge 246 or vice versa).

The first plate 204 has a generally planar form and includes a first surface 204a and an opposing second surface 204b. In an assembled position of the syringe nest assembly 200, the first surface 204a of the plate 204 faces the second surface 206b of the base 206. The first plate 204 further includes a first edge or side 252 and an opposing second edge or side 254. The first and second edges 252, 254 extend parallel to each other. The first plate 204 further includes a third edge or side 256 and an opposing fourth edge or side (not visible in FIGS. 6A-6B). The third edge 256 and the fourth edge extend parallel to each other and perpendicular to the first and second edges 252, 254. A longitudinal axis $X_{204}$ of the first plate 204 extends parallel to the first and second edges 252, 254 from the third edge 256 toward the fourth edge (or vice versa).

The first and second edges 252, 254 of the plate 204 are received and movable within the first and second elongated slots 262, respectively, of the base 206. By this engagement, the first plate 204 is slidable relative to the nest 202, and more particularly the base 206 and chimneys 208.

The first plate 204 further comprises plurality of openings or apertures 260 which extend through the body of the first plate 204, and more particularly from the first surface 204a to the second surface 204b of the first plate 204. The apertures 260 are defined by sidewalls 261 extending through the body of the first plate 204, and more particularly from the first surface 204a to the second surface 204b of the first plate 204. The position of each aperture 260 corresponds to (i.e., is aligned with) a respective one of the chimneys 208 of the nest 202. The apertures 260 may have any geometric shape. Preferably, the apertures 260 are cylindrical (e.g., circular in cross-section). However, it will be understood that the apertures 260 may alternatively be hexagonal or any other shape which complements the shape of the associated chimney 208.

The second plate 280 has a generally planar form and includes a first surface 280a and an opposing second surface 280b. In an assembled position of the syringe nest assembly 200, the first surface 280a of the second plate 280 faces the second surface 204b of the first plate 204. The second plate 280 further includes a first edge or side 286 and an opposing second edge or side 288. The first and second edges 286, 288 extend parallel to each other. The second plate 280 further includes a third edge or side 292 and an opposing fourth edge or side 294. The third and fourth edges 292, 294 extend parallel to each other and perpendicular to the first and second edges 286, 288. A longitudinal axis $X_{280}$ of the second plate 280 extends parallel to the first and second edges 286, 288 from the third edge 292 toward the fourth edge 294 (or vice versa).

The first and second edges 286, 288 of the second plate 280 are also received and movable within the first and second elongated slots 262, respectively, of the base 206. By this engagement, the second plate 280 is slidable relative to the nest 202, and more particularly the base 206 and chimneys 208, and is also slidable relative to the first plate 204.

More particularly, each of the first and second plates 204, 280 is independently slidable in a first direction A or an opposing second direction B relative to the nest 202, the first and second directions being parallel to the longitudinal axis $X_{206}$ of the base 16.

The second plate 280 further comprises plurality of openings or apertures 282 which extend through the body of the second plate 280, and more particularly from the first surface 280a to the second surface 280b of the second plate 280. The apertures 282 are defined by sidewalls 283 extending through the body of the plate second 280, and more particularly from the first surface 280a to the second surface 208b of the second plate 280. The position of each aperture 282 corresponds to (i.e., is aligned with) a respective one of the chimneys 208 of the nest 202 and a respective one of the apertures 260 of the first plate 204. The apertures 282 may have any geometric shape. Preferably, the apertures 282 are cylindrical (e.g., circular in cross-section). However, it will be understood that the apertures 282 may alternatively be hexagonal or any other shape which complements the shape of the associated chimney 208 and aperture 260 of the first plate 204.

While the plates 204, 280 are each preferably configured as a planar rectangular form, the plates 204, 280 can alternatively be configured into any planar fashion suitable for its intended use, such as a planar circular, square, oval, or octagonal shaped form. Preferably, however, the shape of the plates 204, 280 conforms to that of the base 206.

It will be understood by those skilled in the art that the first and second elongated slots 262 of the base 206 need not be formed along the first and second edges 240, 242 of the base 206. Instead, the slots 262 may be formed along the third and fourth edges 244, 246 of the base 206, such that the third and fourth edges 256 and 292, 294 of the first and second plates 204, 280 are received within the slots 262 and slidable in a third or fourth direction which are perpendicular to the first and second directions A, B (i.e., directions perpendicular to the longitudinal axes $X_{206}$ of the base 106).

In a first, assembled position of the syringe nest assembly 200, as shown in FIG. 6A, the first and second plates 204, 280 are coupled to the nest 202, such that the third edge 256 of the first plate 204 and the third edge 292 of the second plate 280 are received within the first elongated slot 262 of the base 206 and the fourth edge of the first plate 204 and the fourth edge 294 of the second plate 280 are received within the second elongated slot 262 of the base 206. As such, the first plate 204, the second plate 280 and the base 206 are movable, and more particularly slidable, relative to each other along the longitudinal axes $X_{204}$, $X_{280}$, $X_{206}$. A syringe (not-shown) is positioned within one or more of the apertures 260, 282 and corresponding chimneys 208 of the assembly 200, in any of the manners described above.

To place the syringe nest assembly 200 in a second position, shown in FIG. 6B, in which the syringes are in the predetermined center to center distance D, the second plate 280 moves, and more particularly, slides in the first direction A along the longitudinal axis $X_{280}$ and the first plate 204 (generally simultaneously) slides in the second direction B along the longitudinal axis $X_{204}$. The sliding movement of the first and second plates 204, 280 in opposite directions (and more particularly in opposite directions towards the syringe) causes the inner sidewalls 261, 283 of the apertures 260, 282 to come into contact with the flange or barrel of the syringe positioned therein. By this contact, the first and second plates 204, 280 center the syringe (i.e., position the syringes according to the requisite center to center distance D) as described above.

In one embodiment, a portion of the base 16, 106, 206 namely at one of the edges, is recessed or indented to form an arcuate shaped edge hole 70, 170, 270. In some embodiments, an arcuate shaped edge ridge 172, 272 may extend generally perpendicularly from the base 16, 106, 206 and surround the edge hole 70, 170, 270. The edge rib 172, 272 (if present) provides stiffness and strength for the base 16, 106, 206 proximate the edge holes 70, 170, 270. Also, in one embodiment, an arcuate shaped hole 71, 174, 284, 290 is formed proximate one or more of the edges of the plate 14, 104, 204, 280. The edge holes 70, 170, 270 of the base 16, 106, 206 are preferably configured to be aligned with the edge holes 71, 174, 284, 290 of the plate 14, 104, 204, 280. One or more edge holes 70, 170, 270, 71, 174, 284, 290 are preferably included in the base 16, 106, 206 and plate 14, 104, 204, 280 such that a user is able to insert a finger or tool or automated equipment is able to grasp the base 16, 106, 206 and/or plate 14, 104, 204, 280 through the edge holes 70, 170, 270, 71, 174, 284, 290 for ease of gripping and moving the plates 14, 104, 204, 280 and/or base 16, 106, 206. The edge holes 70, 170, 270, 71, 174, 284, 290 are not limited to inclusion in the edges of the base 16, 106, 206 and plate 14, 104, 204, 280 and may be instead positioned at nearly any location on the base 16, 106, 206 and plate 14, 104, 204, 280.

Figure 7:
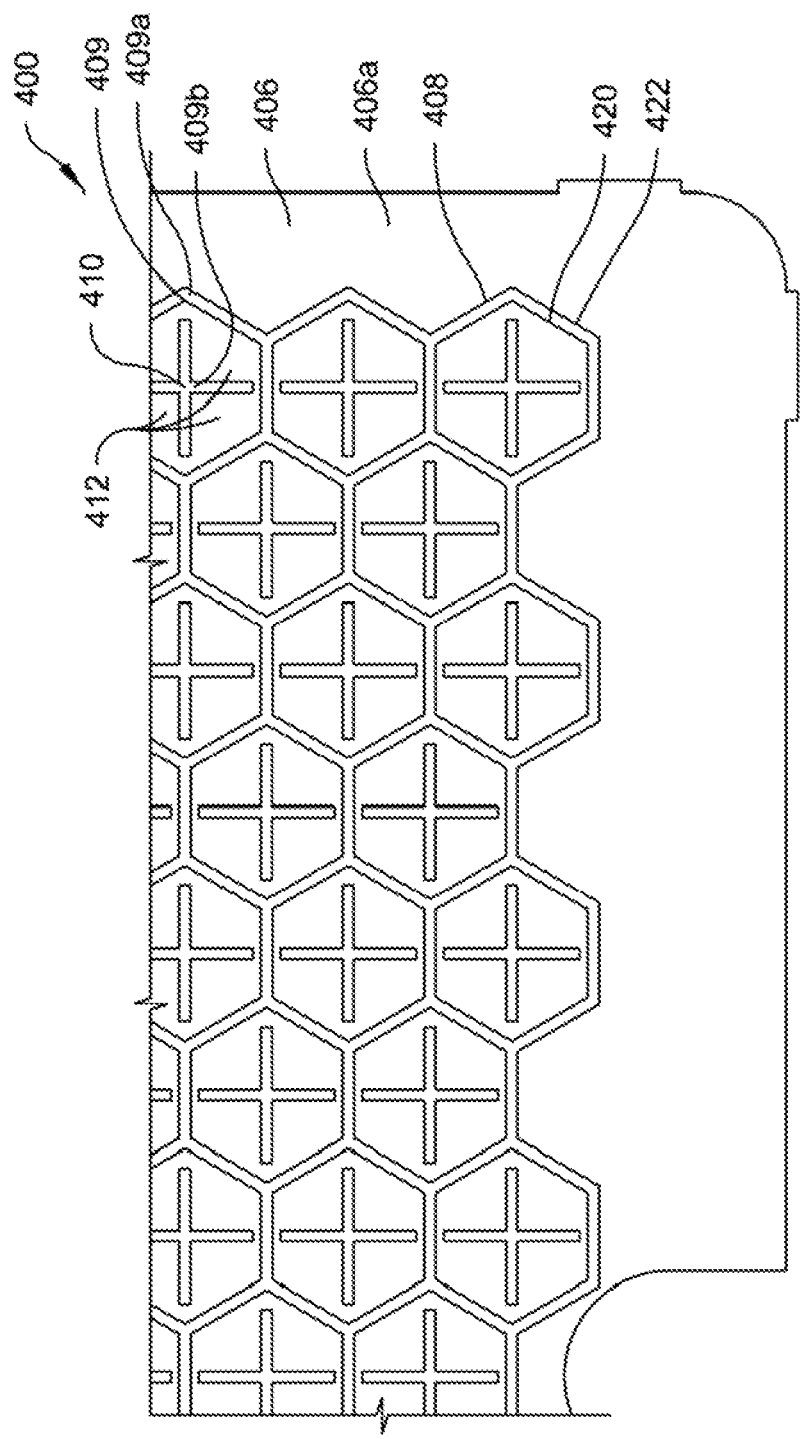
FIG. 7 is a top, partial plan view of a syringe nest assembly in accordance with a fourth embodiment of the present invention.
Figure 8:
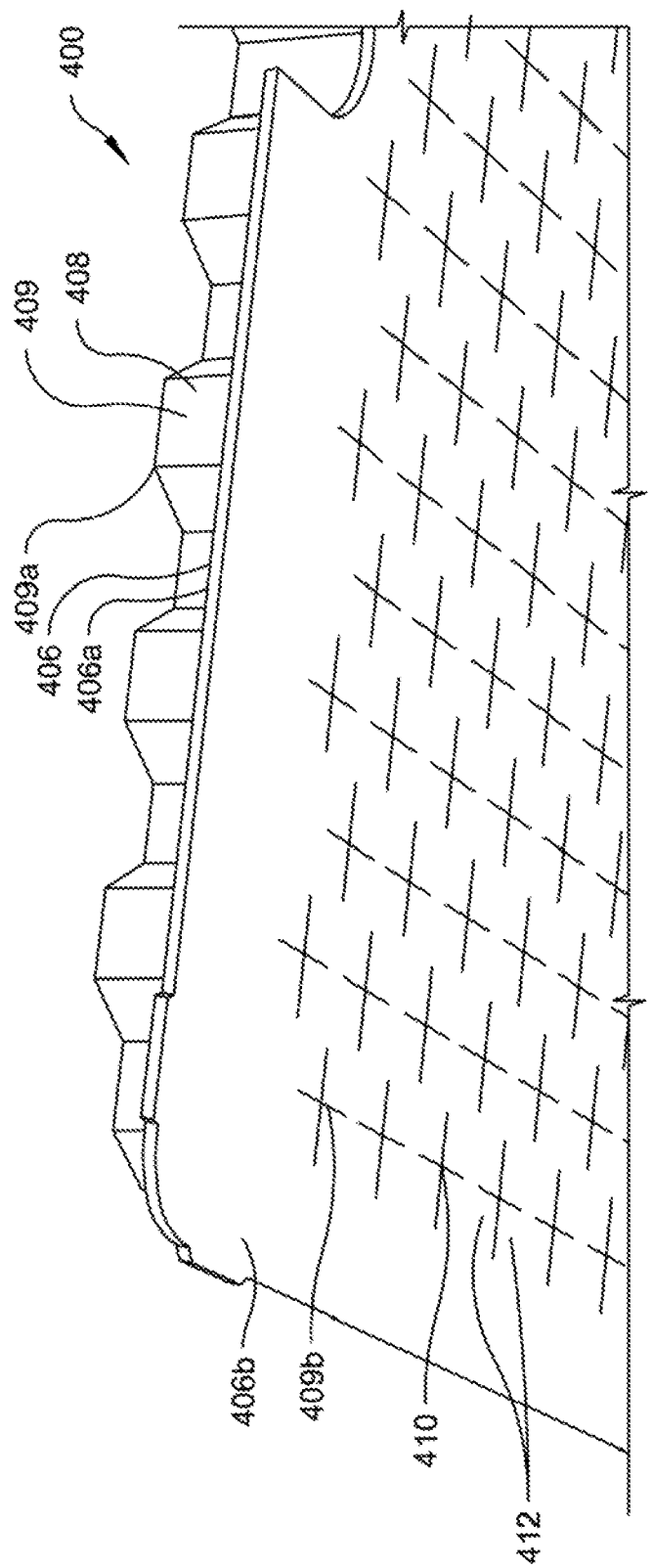
FIG. 8 is a bottom, partial side perspective view of the syringe nest assembly shown in FIG. 7.

Referring to FIGS. 7-8, there is shown another embodiment according to the present invention. The syringe nest assembly 400 of FIGS. 7-8 comprises a syringe nest having a generally planar base or tray 406 having a first surface 406*a* and an opposing second surface 406*b*. Unlike the bases 16, 106, 206 of FIGS. 1-6B, which are generally rigid, the base 406 of FIGS. 7-8 is formed of a relatively flexible material. While the present embodiment is configured with the base 406 configured as a planar rectangular tray, the base 406 can alternatively be configured in any planar fashion suitable for its intended use, such as a planar circular, square, oval, or octagonal shaped tray.

The nest 400 further comprises a plurality of single nesting units, referred to herein as chimneys, 408. Each chimney 408 includes a generally hollow body 409 that extends distally from the first surface 406*a* of the base 406. The hollow body 409 includes a first open end 409*a* distal from the base 16 and a second end 409*b* proximate the base 406. The hollow body 409 also includes an interior wall surface 420 and an exterior wall surface 422. The nest 402 is configured to receive a syringe (not shown) within each of the plurality of chimneys 408.

Referring to FIG. 7, in one embodiment, each of the chimneys 408 preferably has a hexagonal shape or geometry, and the hexagonal chimneys 408 are arranged in a honeycomb pattern, as described above with respect to FIGS. 1-3B. It will, however, be understood that the chimneys 408 need not have a hexagonal geometry and need not be arranged in a honeycomb pattern. Indeed, the chimneys 408 may be cylindrical and arranged in any pattern, with or without gaps or voids between adjacent chimneys.

At the proximate end 409*b* of each chimney 408, the flexible base 406 includes a selectively openable/closable notch 410. Preferably, the notch 410 is formed by a pair of cross-cuts made in the material of the flexible base 406. As such, the proximate end 409*b* of each chimney 408 includes four flaps 412 of the flexible base 406 material formed by the cross-cuts.

Each notch 410 is in a closed position, as shown in FIGS. 7-8, when no syringe is positioned within the chimney 408. However, when a syringe is placed within the chimney 408, the barrel of the syringe extends through the hollow body 409 of the chimney 408 and through the flexible base 406 at the notch 410. As such, the notch 410 is placed in an open position, wherein the flaps 412 surround and resilient grip the syringe barrel, thereby centering or stabilizing the syringe to achieve the predetermined center to center distance between adjacent syringes.

The base 406 may be formed of any flexible material. Preferably, the base 406 is a thin film of polypropylene or is formed of a thermoplastic elastomer that is bonded to the bottom of the chimneys 408 via heat staking, ultrasonic welding, laser welding, and the like, or is integrally formed with the chimneys 408.

It will be appreciated by those skilled in the art that changes could be made to the embodiments described above without departing from the broad inventive concept thereof. It is to be understood, therefore, that the present invention is not limited to the particular embodiments disclosed, but it is intended to cover modifications within the spirit and scope of the appended claims.

We claim:

1. A syringe nest assembly comprising:
a base having a first surface and an opposing second surface, the base comprising a plurality of nesting units extending upwardly away from the first surface of the base, each nesting unit comprising a hollow body having a first open end distal from the first surface of the base and an opposing second open end;
a first plate movably coupled to the base, the first plate having a generally planar form, a first surface and an opposing second surface, the first plate being slidable relative to the base along a longitudinal axis parallel to edges of the base, the first plate comprising a plurality of apertures extending from the first surface to the second surface of the first plate, each aperture of the first plate being generally aligned with a respective nesting unit of the base; and
a syringe positioned within at least two adjacent apertures of the plurality of apertures,
wherein sliding of the first plate relative to the base results in centering of the syringes.

2. The syringe nest assembly of claim 1, wherein each nesting unit has a hexagonal hollow body.

3. The syringe nest assembly of claim 2, wherein the nesting units are arranged in a honeycomb pattern.

4. The syringe nest assembly of claim 1, wherein each nesting unit has a cylindrical hollow body.

5. The syringe nest assembly of claim 1, wherein the second surface of the first plate faces the first surface of the base.

6. The syringe nest assembly of claim 1,
wherein the base has a first edge and an opposing second edge,
wherein the first plate has a first edge and an opposing second edge, and
wherein, proximate the first edges, one of the base and the first plate includes an elongated slot and the other of the base and the first plate includes at least one protrusion configured to be slidably received within the elongated slot.

7. The syringe nest assembly of claim 6, wherein the first plate includes the elongated slot and the base includes the at least one protrusion, and wherein the at least one protrusion is an outwardly protruding flange formed at the first open end of at least one of the nesting units proximate the first and second edges of the base.

8. The syringe nest assembly of claim 6, wherein the base includes the elongated slot and the first plate includes the at least one protrusion, and wherein the at least one protrusion is a post extending downwardly away from the second face of the first plate toward the first face of the base.

9. The syringe nest assembly of claim 1, wherein the first surface of the first plate faces the second surface of the base.

10. The syringe nest assembly of claim 1,
wherein the base has a first edge and an opposing second edge, wherein the first plate has a first edge and an opposing second edge, wherein, proximate the first edges, one of the base and the first plate includes an elongated slot, and wherein the first edge of the other of the base and the first plate is configured to be slidably received within the elongated slot.

11. The syringe nest assembly of claim 10, wherein the base includes the elongated slot.

12. The syringe nest assembly of claim 1, further comprising a second plate movably coupled to the base, the second plate having a generally planar form, a first surface and an opposing second surface, the second plate comprising a plurality of apertures extending from the first surface to the second surface of the second plate, each aperture of the second plate being generally aligned with a respective nesting unit of the base and a respective aperture of the first plate.

13. The syringe nest assembly of claim 12, wherein the first surface of the first plate faces the second surface of the base and wherein the first surface of the second plate faces the second surface of the first plate.

14. The syringe nest assembly of claim 13,
wherein the base has a first edge and an opposing second edge,
wherein the first plate has a first edge and an opposing second edge,
wherein the second plate has a first edge and an opposing second edge,
wherein the base includes an elongated slot proximate its first edge, and wherein the first edge of the first plate and the first edge of the second plate are slidably received within the elongated slot.

15. The syringe nest assembly of claim 14, wherein the first plate and the second plate are slidable in opposite directions of each other with respect to the base.

* * * * *